United States Patent
Aris et al.

(10) Patent No.: US 9,815,912 B2
(45) Date of Patent: Nov. 14, 2017

(54) HYDROPHILIC MODIFICATION OF WATER INSOLUBLE POLYSACCHARIDE AS SURFACE-ACTIVE AGENTS

(71) Applicants: Zarif Farhana Mohd Aris, Lowell, MA (US); Ryan M. Bouldin, Bar Harbor, ME (US); Ramaswamy Nagarajan, Westford, MA (US); Bridgette Budhlall, Dracut, MA (US); Vishal Bavishi, Lowell, MA (US)

(72) Inventors: Zarif Farhana Mohd Aris, Lowell, MA (US); Ryan M. Bouldin, Bar Harbor, ME (US); Ramaswamy Nagarajan, Westford, MA (US); Bridgette Budhlall, Dracut, MA (US); Vishal Bavishi, Lowell, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 13/841,903

(22) Filed: Mar. 15, 2013

(65) Prior Publication Data

US 2014/0045218 A1 Feb. 13, 2014

Related U.S. Application Data

(60) Provisional application No. 61/612,909, filed on Mar. 19, 2012.

(51) Int. Cl.
- *C08B 37/00* (2006.01)
- *C08B 37/08* (2006.01)
- *C12P 19/26* (2006.01)

(52) U.S. Cl.
CPC .......... *C08B 37/0045* (2013.01); *C08B 37/00* (2013.01); *C08B 37/003* (2013.01); *C08B 37/0084* (2013.01); *C12P 19/26* (2013.01)

(58) Field of Classification Search
None
See application file for complete search history.

(56) References Cited

U.S. PATENT DOCUMENTS

| | | | |
|---|---|---|---|
| 5,384,400 A * | 1/1995 | Crescenzi et al. | 536/2 |
| 2009/0048412 A1 * | 2/2009 | Soula et al. | 527/200 |
| 2010/0167991 A1 * | 7/2010 | Soula et al. | 514/8 |

* cited by examiner

*Primary Examiner* — Layla Berry
(74) *Attorney, Agent, or Firm* — Milstein Zhang & Wu LLC

(57) ABSTRACT

A surfactant produced by reacting naturally occurring polysaccharides that are not water soluble with a hydrophilic substituent on a carboxylic portion of the polysaccharide. In a second reaction, the surfactant is further substituted on a hydroxylic portion with a hydrophobic or lipophilic substituent, so as to make the reaction product both water soluble and capable of attracting oily material that is hydrophobic to be removed from a substrate by cleaning in water. Methods of making the surfactant and the follow-on reaction product are described.

12 Claims, 9 Drawing Sheets

$R_1$ = COOH, CH$_2$OH, OH, NH$_2$ $R_2$ = COOH, CH$_2$OH, OH, NH$_2$ $R_1$ = COOH, CH$_2$OH, OH, NH$_2$ $R_2$ = COOH, CH$_2$OH, OH, NH$_2$

FIG. 2A
FIG. 2B
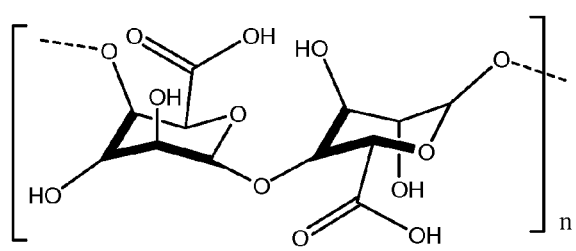
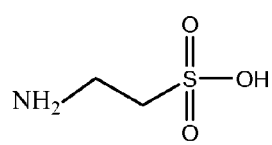
Polygalacturonic Acid (PGA)
2-aminoethanesulfonic acid
EDCL
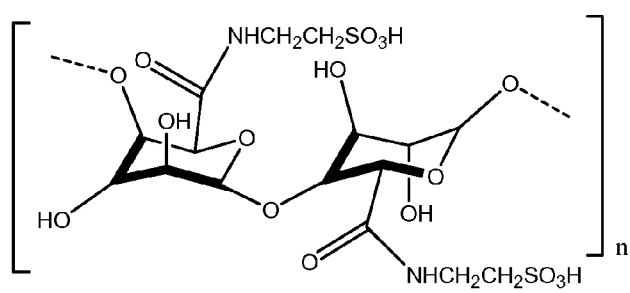
Polygalacturonic Acid Sulphonate (PGA-SO$_3$)
FIG. 2C Polygalacturonic Acid Amino Terminated PEG Methyl Ether PGA - PEG Derivative

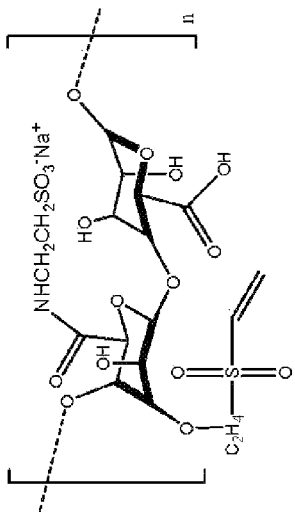
Polygalacturonic Acid (PGA)
FIG. 8A
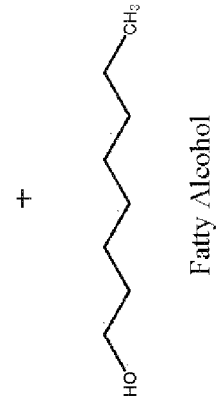
Divinyl Sulfone (DVS)
FIG. 8B
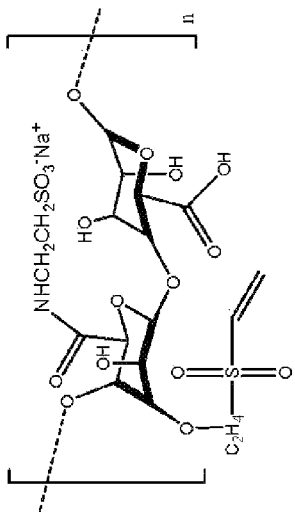
PGA-DVS
FIG. 8C
Fatty Alcohol
FIG. 8D
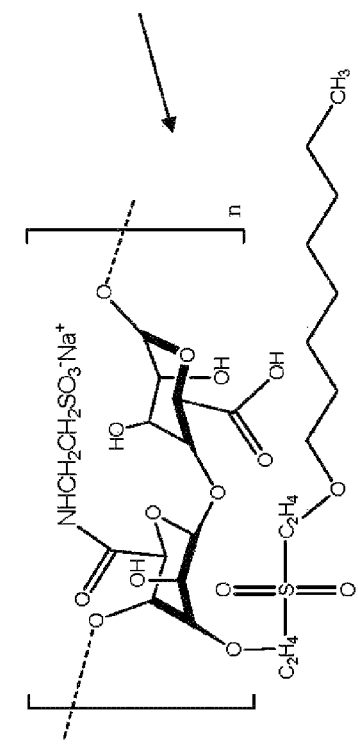
PGA-DVS-Fatty Alcohol
FIG. 8E

HYDROPHILIC MODIFICATION OF WATER INSOLUBLE POLYSACCHARIDE AS SURFACE-ACTIVE AGENTS

CROSS-REFERENCE TO RELATED APPLICATIONS

This application claims priority to and the benefit of co-pending U.S. provisional patent application Ser. No. 61/612,909, filed Mar. 19, 2012, which application is incorporated herein by reference in its entirety.

THE NAMES OF THE PARTIES TO A JOINT RESEARCH AGREEMENT

NOT APPLICABLE.

INCORPORATION-BY-REFERENCE OF MATERIAL SUBMITTED ON A COMPACT DISC

NOT APPLICABLE.

FIELD OF THE INVENTION

The invention relates to surfactants in general and particularly to surfactants that are biocompatible and nontoxic.

BACKGROUND OF THE INVENTION

Surface-active polymers derived from naturally occurring polysaccharides have applications in numerous areas, including detergents, cosmetic, and pharmaceutical products. In these products, the role of the surfactant is to lower the interfacial surface tension between dissimilar phases therefore improving compatibility of the phases. Surfactants can act as emulsifiers, stabilizers, wetting aid and also assist in cleaning processes.

In the cleaning products industry, soaps based on natural oils were very common several decades ago. With the advent of high performance detergents, the use of soaps derived from bio-based oils has declined considerably. The newer detergents are often non-biodegradable and can cause serious environmental problems. See for example, U.S Environmental Protection Agency, Nonylphenol (NP) and Nonylphenol ethoxylates (NPEs) Action Plan, RIN 2070-ZA09, 2010; Hoponick, Nonylphenol Ethoxylates: A Safer Alternative Exists to this Toxic Cleaning Agent. Sierra Club, 2005; and European Union. 4-Nonylphenol (branched) and Nonylphenol Risk Assessment Report. Institute for Health and Consumer Protection, European Chemical Bureau, Vol. 10, 2002.

With the goal of producing surface-active compounds from bio-based feedstock, several synthetic strategies have been reported. See for example, Stevens C. V et al., Polymeric Surfactants Based on Inulin, a Polysaccharide extracted from Chicory: Synthesis and Interfacial Properties, Biomacromolecules, Volume: 2 (4), pp 1256-1259, 2001; Yuping Wei et al., Amphiphilic cellulose: Surface activity and aqueous self-assembly into nano-sized polymeric micelles, Reactive & Functional Polymers 68, pp 981-989, 2008; Tianhong Zhang et al., Novel Polysaccharide Surfactants: Synthesis of Model: Compounds and Dextran-Based Surfactants and Dextran-Based Surfactants, Macromolecules, 27 (25), pp. 7302-7308, 1994; Pan Hong et al., Surface properties and synthesis of the cellulose-based amphoteric polymeric surfactant, Carbohydrate Polymers 69, pp. 625-630, 2007; and Alain Durand et al., Neutral amphiphilic polysaccharides: chemical structure and emulsifying properties, Colloid. Polym. Sci., 284: 536-545, 2006.

Polysaccharides are typically a common starting material for these surfactants, because they represent the most abundantly available bio-based, renewable feedstock in the world. Typically, polysaccharides have to be modified by a variety of synthetic chemical methods to yield surface-active properties. Several methods are available for the preparation of these polysaccharide derivatives. Some common derivatives include various alkyl ether derivatives (carboxymethyl cellulose, hydroxyethyl cellulose (U.S. Pat. No. 3,498,971 issued Mar. 3, 1970 to Blaga et al.), hydroxypropyl cellulose), polysaccharides modified with amphiphilic hydrocarbons, and glucose ethers as exemplified by U.S. Pat. No, 3,574,188 issued Apr. 6, 1971 to Takehara et al., U.S. Pat. No. 6,620,295 issued Sep. 16, 2003 to Shannon et al., and U.S. Pat. No. 2,974,134 issued Mar. 7, 1961 to Pollitzer, respectively.

In all of these cases, water-soluble polysaccharides are hydrophobically modified to yield amphiphilic molecules. Unfortunately, in some cases, the modifications require harsh reaction conditions that commonly lead to partial or substantial degradation of the polysaccharide. To date, the bulk of the research reported has been on either converting water-soluble polysaccharides into surface-active agents by attaching hydrophobic entities or multiple step conversions of water insoluble polysaccharides into soluble surfactants. It is therefore desirable to employ synthetic strategies that involve milder conditions (to preserve structural integrity) to yield amphiphilic products that are efficient surfactants.

Due to toxicity and environmental concerns, the use of nonylphenol ethoxylates is being phased out in several countries across the globe. Therefore, there is a need to create anew class of effective surfactants that can serve as drop-in replacements for NPEs.

SUMMARY OF THE INVENTION

The basic premise of the invention is the use of polysaccharides as a backbone such that the hydrophilic-lipophilic balance can be tailored by attaching first (1) hydrophilic groups followed and if necessary, (2) attachment of hydrophobic groups. The hydrophobic segments of the modified polysaccharide solubilize/emulsify oily dirt, while the hydrophilic segments help wash the emulsified dirt-surfactant complex into the aqueous phase, thus accomplish the cleaning process.

Since the polysaccharides and the hydrophilic groups (taurine, polyethylene glycol) are all biocompatible, biodegradable and not toxic, it is expected that the surfactants produced using the combination of these materials are also expected to be non-toxic and biocompatible.

This invention relates to creating a new class of surface-active agents (amphiphilic molecules) from naturally occurring polysaccharides. The starting materials used in this invention are either partially water-soluble or completely insoluble polysaccharides. They were hydrophilically modified to yield effective wetting agents or emulsifiers. See examples 1-7 for methods of hydrophilically modifying water insoluble polysaccharide. See example 1 and Table 1 for surface tension results. In one of the embodiments, the hydrophilic modification involves covalent functionalization of the polygalacturonic acid using naturally occurring or synthetic molecules that may include but are not restricted to amino acids, peptides, and lipids containing sulfonate groups, and/or polyethylene glycol (PEG) or polypropylene glycol (PPG) homopolymers and copolymers. In another embodiment the said modification process can be carried out with conventional chemical methods using heat supplied using conventional means or using microwave radiation, in the presence of chemical or enzyme catalyst, or by some combination of these methods. See examples 1-9.

Usage of surfactants in detergents, cosmetics and other such applications require specific surface activity which can be controlled by controlling the hydrophilic and lipophilic/hydrophobic balance (HLB). For achieving such a controlled HLB the hydrophilically modified surfactant may be further hydrophobically modified in the subsequent steps, depending on the application intended. See Examples 8-9 for hydrophobic modification of hydrophilically modified polysaccharide. In one of the embodiments the hydrophobic modification is performed using Divinyl Sulphone (DVS) which is then post reacted to include hydrophobic moieties. In yet another embodiment these modified polysaccharides are further hydrophobically modified with naturally occurring fatty alcohols that includes but are not restricted to saturated fatty alcohols of chain length varying from $C_5$ to $C_{22}$. See example 9.

This new class of hydrophilically and/or hydrophobically modified polysaccharides was found to unexpectedly and dramatically improve surface activity to levels comparable to that of NPEs and other synthetic/natural surfactants. They also show good acid/base stability and comparable cleaning and stain removing ability when compared to synthetic/natural surfactants. See example 1 for surface-active properties studies. See example 10 for acid/base stability study. See examples 11 and 12 for cleaning efficacy and stain removal ability respectively.

It is believed this new class of polysaccharides can be used as a drop-in replacement in several commercial applications including detergents, cosmetics, and pharmaceuticals.

According to one aspect, the invention features a composition of matter. The composition of matter comprises a reaction product of a naturally occurring polysaccharide having a backbone structure comprising a plurality of monomer units, each monomer unit having at least one of a carboxylic group or an amine group and having at least one hydroxyl group; and a hydrophilic moiety configured to react with some of said at least one of a carboxylic group or an amine group of said naturally occurring polysaccharide; said reaction product retaining said backbone structure and having surface active properties in liquids.

In one embodiment, the naturally occurring polysaccharide is a water insoluble polysaccharide.

In another embodiment, the water insoluble polysaccharide is a polysaccharide derivative of polygalacturonic acid.

In yet another embodiment, the water insoluble polysaccharide is a polysaccharide derivative of alginic acid.

In another embodiment, the water insoluble polysaccharide is a polysaccharide derivative of chitosan.

In still another embodiment, the hydrophilic moiety is selected from the group of materials consisting of amino acids, peptides, and lipids containing sulfonate groups, polyethylene glycol (PEG) or polypropylene glycol (PPG), taurine, and homopolymers and copolymers thereof.

In a further embodiment, the composition of matter comprises a further reaction product retaining the backbone structure and having some of the at least one hydroxyl group the naturally occurring polysaccharide substituted with a hydrophobic or lipophilic moiety.

In yet a further embodiment, the hydrophobic or lipophilic moiety is divinylsulphone.

In an additional embodiment, the hydrophobic or lipophilic moiety is a naturally occurring fatty alcohol.

In one more embodiment, the naturally occurring fatty alcohol is a selected one of lauryl alcohol, stearyl alcohol, and a saturated fatty alcohol of chain length in the range from $C_5$ to $C_{22}$.

According to another aspect, the invention relates to a method of making a composition of matter. The method comprises the steps of providing a naturally occurring polysaccharide having a backbone structure comprising a plurality of monomer units, each monomer unit having at least one of a carboxylic group or an amine group and having at least one hydroxyl group; reacting the naturally occurring polysaccharide with a hydrophilic moiety that substitutes for some of the at least one of a carboxylic group or an amine group of the naturally occurring polysaccharide; and recovering a reaction product that retains the backbone structure and is surface active in liquids.

In one embodiment, the naturally occurring polysaccharide is a water insoluble polysaccharide.

In another embodiment, the water insoluble polysaccharide is a polysaccharide derivative of polygalacturonic acid.

In yet another embodiment, the water insoluble polysaccharide is a polysaccharide derivative of alginic acid.

In another embodiment, the water insoluble polysaccharide is a polysaccharide derivative of chitosan.

In still another embodiment, the reacting step is performed using applied microwave energy.

In a further embodiment, the reacting step is performed using thermal energy.

In still a further embodiment, the reacting step involves a catalyst.

In yet a further embodiment, the hydrophilic moiety is selected from the group of materials consisting of amino acids, peptides, and lipids containing sulfonate groups, polyethylene glycol (PEG) or polypropylene glycol (PPG), taurine, and homopolymers and copolymers thereof.

In an additional embodiment, the method of making a composition of matter further comprises the steps of reacting the reaction product that retains the backbone structure with a hydrophobic or lipophilic moiety that substitutes for sonic of the at least one hydroxyl group of the naturally occurring polysaccharide; and recovering a second reaction product that retains the backbone structure and has both hydrophilic and hydrophobic/lipophilic properties.

In still a further embodiment, the hydrophobic or lipophilic moiety is a naturally occurring fatty alcohol.

In another embodiment, the naturally occurring fatty alcohol is a selected one of lauryl alcohol, stearyl alcohol, and a saturated fatty alcohol of chain length in the range from $C_5$ to $C_{22}$.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 2A, FIG. 2B, FIG. 2C is a schematic chemical diagram that shows a chemical synthesis reaction for hydrophilic modification of polygalacturonic acid and alginic acid.

FIG. 8A, FIG. 8B, FIG. 8C, FIG. 8D, FIG. 8E is a diagram that shows a chemical synthesis reaction for hydrophilic/hydrophobic modification of polygalacturonic acid prepared using sulphonate, DVS, and fatty alcohol.

DETAILED DESCRIPTION

The purpose of this invention is to provide a viable alternative to the non-ionic surfactants, nonyl phenol ethoxylates (NPEs), NPE's are known to be endocrine disruptors and estrogen mimics upon degradation. NPEs are listed on the Environmental Protection Agency (EPA) Chemicals of High Concern list due to their environmental persistent, bio-accumulative nature, and toxicity. Therefore, there is need for safer alternative surface-active compounds that can be used to lower surface tension, aid wetting and emulsify mixtures. The goal of this work has been to develop a series of polymeric surfactants that are bio-based (specifically based on natural polysaccharides) and have surface activity comparable to NPEs when used at low concentrations.

In this disclosure, we report an environmentally friendly method for the modification of water insoluble (hydrophobic) polysaccharides. The resulting products are bio-based surfactants. Most of the commercially used synthetic and bio-based surfactants are based on water-soluble (hydrophilic) polysaccharides, which are hydrophobically modified to yield amphiphilic moieties. There are several shortcomings in current approaches, including the methods employed in the chemical synthesis. In order to obtain surface-active products, these processes often rely on harsh chemical reactions involving toxic solvents and reagents. These conditions, however commonly lead to partial or substantial degradation of the polysaccharides. It is therefore desirable to have available derivatization methods, which employ mild conditions to yield products that are also sufficiently efficient to be applicable to industrial scale use.

Though synthetic surfactants serve as good cleaning agents offering desired cleaning and detergency effect, they pose major toxicity issues with several deleterious effects in aquatic life. Extensive research have shown that nonyl phenol ethoxylates (NPEs), mimic natural hormones, disrupting the endocrine and developmental systems of fish, shellfish and other aquatic species. NPEs are particularly dangerous because they become more toxic as they are metabolized by bacteria. Owing to all the above-mentioned drawbacks, there is an immediate need for developing non-toxic, bio-based and preferable biodegradable surfactants. Our invention is aimed at developing a new class of bio-based surfactants through an environment friendly, green synthetic route. The accomplishment of the invention is the synthesis of a non-toxic surfactant using benign ways without compromising on the performance (surface activity).

Figure 1A:
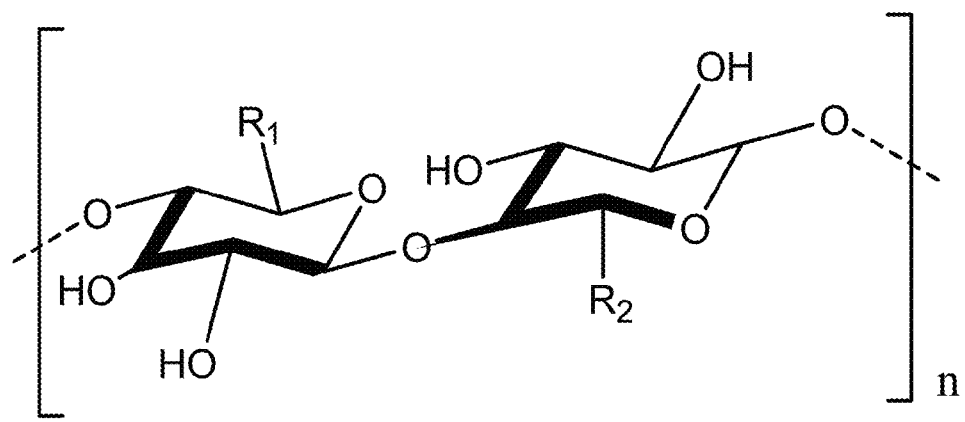
FIG. 1A is a schematic chemical diagram that shows structure examples of various water-insoluble naturally occurring polysaccharides.
Figure 1B:
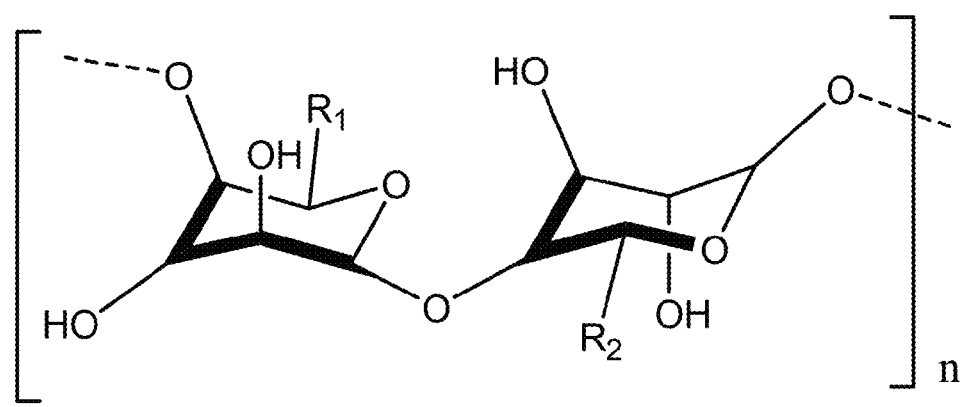
FIG. 1B is a schematic chemical diagram that shows naturally occurring polysaccharides having structural formulae as shown.

The present disclosure describes a new class of surface-active polymers derived from naturally occurring polysaccharides having structural formulae as shown in FIG. 1A and FIG. 1B that is modified by covalent attachment of hydrophilic moieties (both synthetic and bio-based). See example 2, 6 and 7.

EXAMPLE 1

Chemical Synthesis of Surface-Active, Water Soluble Polygalacturonic Acid Derivative:

Water-insoluble polygalacturonic acid (3.125 mmol) in deionized water (30 mL) was mixed with naturally occurring amino acid, taurine (2-aminoethanesulfonic acid) (3.125 mmol) and EDCL, 1-ethyl-3-(3-dimethylaminopropyl)carbodiimide (3.125 mmol) as the coupling agent and excess sodium bicarbonate ($NaHCO_3$) was added under stirring. After a 24-hour reaction, a water-soluble product containing the surface-active modified polysaccharide was formed. The unreacted starting materials remain insoluble. These products were separated out by filtration. The water-soluble product was dialyzed using a Spectra/Pore dialysis membrane (molecular weight cut off of 10,000) for 3 days to remove salts and unreacted small molecules. Surface-active polygalacturonic acid derivatives were obtained as a mild-yellowish solid by removal of water using a rotary evaporator or by freeze-drying.

Figure 3:
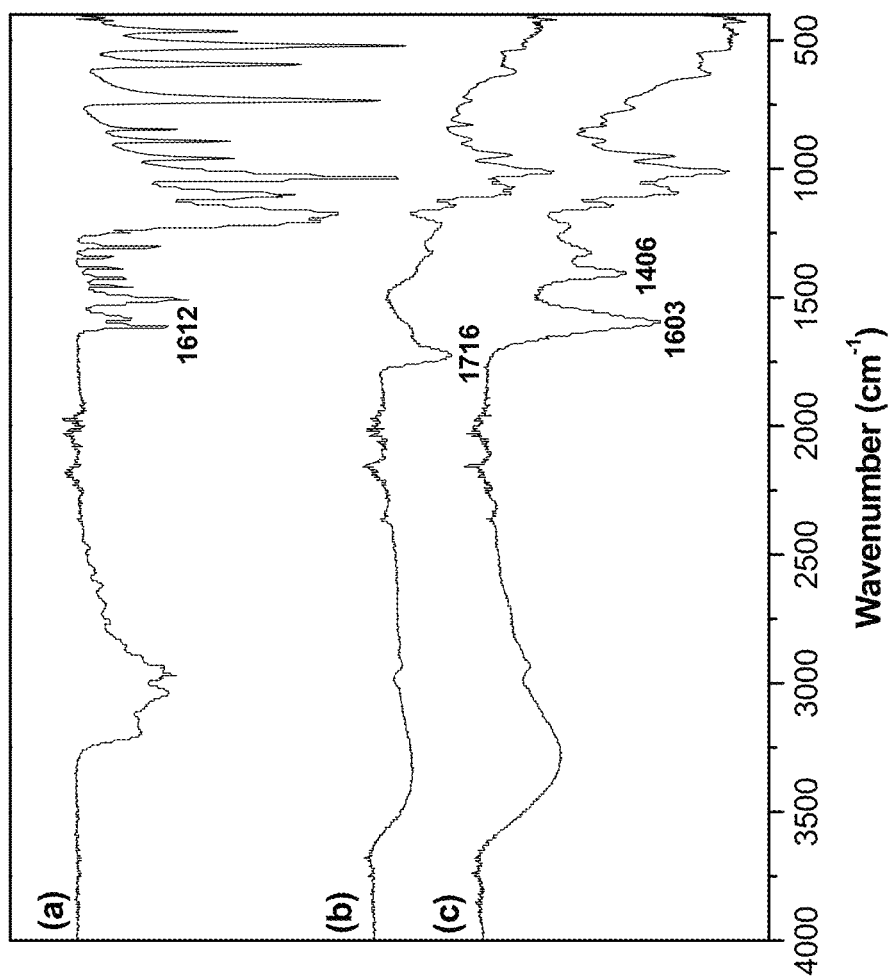
FIG. 3 is a diagram that shows FTIR spectra of control (unmodified) polygalacturonic acid and derivatives (modified with taurine) of polygalacturonic acid.

FIG. 3 shows an FTIR spectrum of unmodified and functionalized polygalacturonic acid derivative synthesized through EDCL coupling technique. In FIG. 3 the curves are the FTIR spectra of (a) 2-aminoethanesulfonate (Taurine), (b) Unmodified Polygalacturonic acid and (c) Polygalacturonic sulphonate.

Polysaccharide Derivative Demonstrates Surface-Active Properties:

Table 1 shows the surface-activity properties of unmodified and modified polysaccharides, which were compared to commercial surfactants sodium lauryl sulfate (SLS) and nonyl phenol ethoxylates (Triton X-100)

TABLE 1

| Surface tension of unmodified and modified polysaccharides | |
|---|---|
| | Surface Tension (mN/m) |
| Deionized Water | 73.02 |
| Sodium Lauryl Sulfate (SLS) | 33.52 |
| Nonylphenol Ethoxylates (Triton ™ X-100) | 31.87 |
| Unmodified Polygalacturonic Acid | 61.64 |
| Unmodified Taurine | 65.64 |
| Polygalacturonic Acid Derivative | 33.49 |

TABLE 1-continued

Surface tension of unmodified and modified polysaccharides

| | Surface Tension (mN/m) |
|---|---|
| Unmodified Alginic Acid | 64.30 |
| Alginic acid Derivative | 36.08 |

*Measured in 0.1% analyte concentration at 24° C. using Du Noüy ring method

Degree of Functionalization of Surface-Active, Water-Soluble Polygalacturonic Acid Derivative:

The polygalacturonic acid derivatives prepared according to Example 1 characterized by elemental analysis shows the surface-active polysaccharides have at least a 10% functionalization.

TABLE 2

Elemental analysis and degree of amidation (DA) of PGA-SO$_3$

| Molar Ratio | Element | | | | DA % |
|---|---|---|---|---|---|
| | C | H | N | S | |
| 1:1.4 | 33.93 | 4.00 | 0.49 | 1.067 | 10.0 |
| 1:2.8 | 33.54 | 4.07 | 0.52 | 1.22 | 10.6 |
| 1:4.2 | 33.62 | 4.02 | 0.53 | 1.231 | 10.82 |

EXAMPLE 2

Chemical Synthesis of Surface-Active, Water Soluble Alginic Acid Derivative:

Water insoluble alginic acid (3.125 mmol) deionized water (30 mL) was mixed with taurine (2-aminoethanesulfonic acid) (3.125 mmol) and EDCL (1-ethyl-3-(3-dimethylaminopropyl)carbodiimide) (3.125 mmol) as the coupling agent and excess sodium bicarbonate (NaHCO$_3$) was added under stirring. After a 24-hour reaction, a water-soluble product containing the surface-active modified polysaccharide was formed. The unreacted starting materials remain insoluble. These products were separated out by filtration. The water-soluble product was dialyzed using a Spectra/Pore dialysis membrane (molecular weight cut off of 50,000) for 3 days to remove salts and unreacted EDCL. Surface-active alginic acid derivatives were obtained as an off-white solid by removal of water using a rotary evaporator or by freeze-drying.

Figure 4:
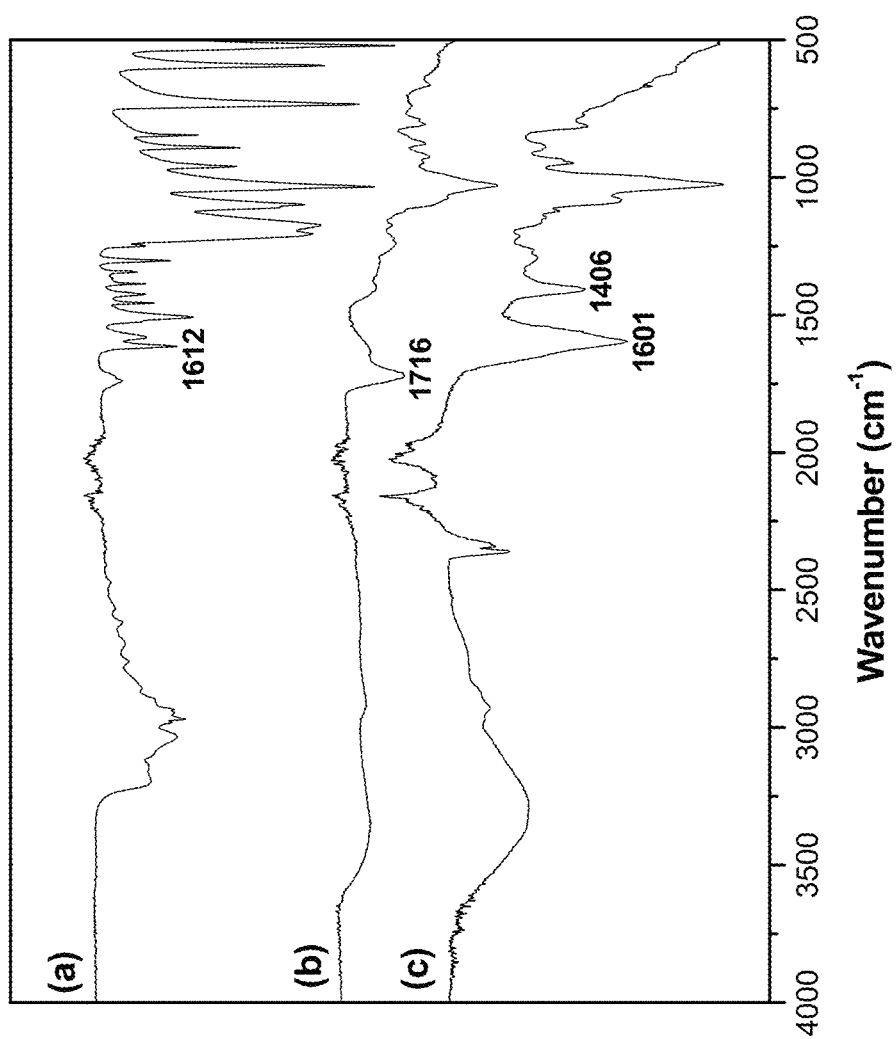
FIG. 4 is a diagram that shows FTIR spectra of unmodified alginic acid and derivatives of alginic acid based surfactants.

FIG. 4 shows an FTIR spectrum of unmodified and functionalized alginic acid derivative synthesized through EDCL coupling technique. In FIG. 4 the curves are the FTIR spectra of (a) 2-aminoethanesulfonate (Taurine), (b) Unmodified Alginic acid and (c) Alginic sulphonate.

EXAMPLE 3

Enzymatic Synthesis of Surface-Active, Water Soluble Polygalacturonic Acid Derivative:

Water-insoluble polygalacturonic acid (PGA) (1 mmol) and taurine (2-aminoethanesulfonic acid) (1 mmol) was added to a 10 mL round bottom flask. Approximately 10 wt % of total reactants of immobilized lipase B (Novozyme® 435) was used as an enzyme catalyst for the amidation of PGA. The reaction was performed in 5 mL low molecular weight polyethylene glycol (PEG) as a solvent. The reaction was heated in an oil bath at 80° C. for 6, 12, 24 and 72 hours.

EXAMPLE 4

Microwave-assisted Synthesis of Surface-Active, Water Soluble Polygalacturonic Acid Derivative:

0.250 mmol of polygalacturonic acid, 0.250 mmol of taurine (2-aminoethanesulfonic acid) was added to a 0.2-0.5 mL biotage vial. After 30 min reaction, water-soluble product was formed. The unreacted reactants remained water-insoluble and were filtered out. The water-soluble product was dialyzed using a Spectra/Pore dialysis membrane (molecular weight cut off of 10,000) for 3 days. The mild yellow polygalacturonic acid derivative was obtained by removing the water using rotary evaporator or by freeze-drying.

Figure 5:
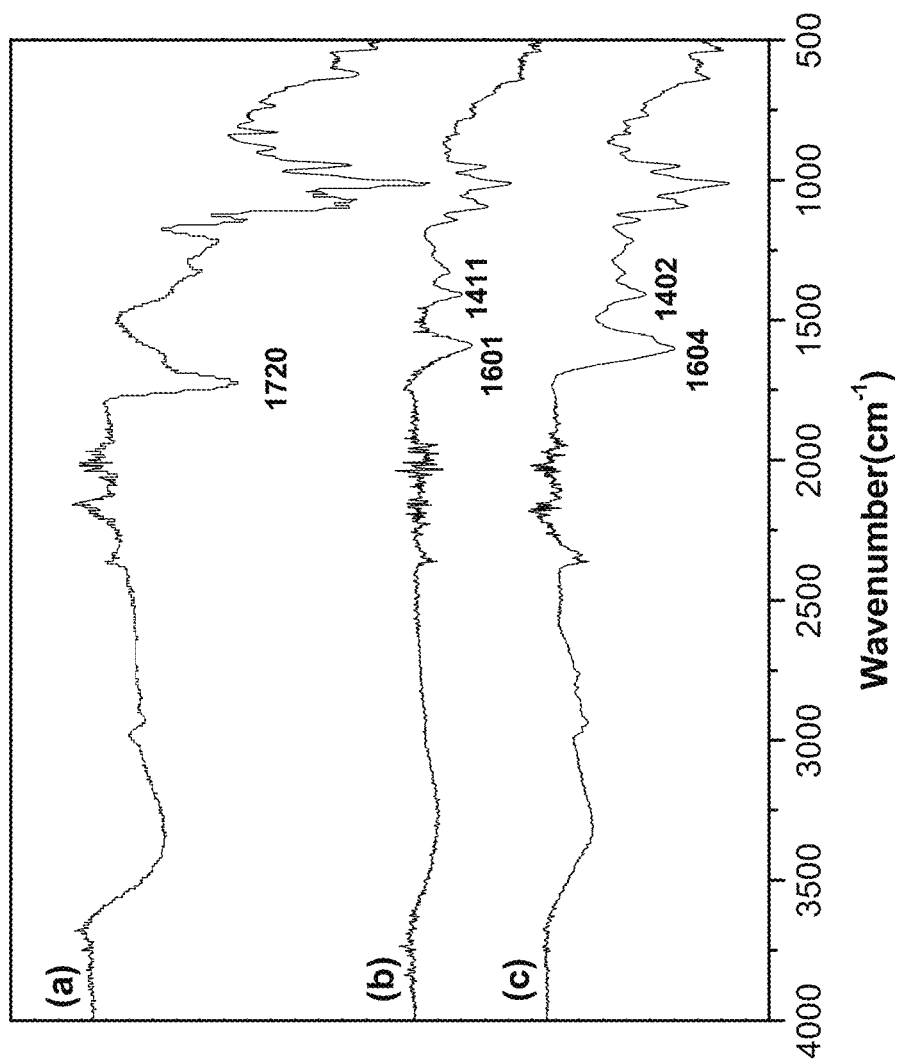
FIG. 5 is a diagram that shows FTIR spectrum of modified PGA sulphonate synthesized by conventional method and microwave synthesis.

FIG. 5 shows an FTIR spectrum of unmodified and functionalized polygalacturonic acid derivative synthesized through microwave-assisted synthesis. In FIG. 5 the curves are the FTIR spectra of (a) Unmodified PGA, and PGA-sulphonate synthesized using (b) Conventional method (c) Microwave synthesis.

EXAMPLE 5

Microwave Synthesis of Surface-Active, Water Soluble Alginic Acid Derivative:

0.250 mmol of alginic acid and 0.250 mmol of taurine (2-aminoethanesulfonic acid) was added to a 0.2-0.5 mL biotage microwave reactor vial. After a 30 min reaction, a water-soluble product containing the surface-active modified polysaccharide was formed. The unreacted starting materials remain insoluble and were filtered out. The water-soluble product was dialyzed using a Spectra/Pore dialysis membrane (molecular weight cut off of 50,000) for 3 days. The off-white alginic acid derivative was obtained by removing the water using rotary evaporator or by freeze-drying.

Figure 6:
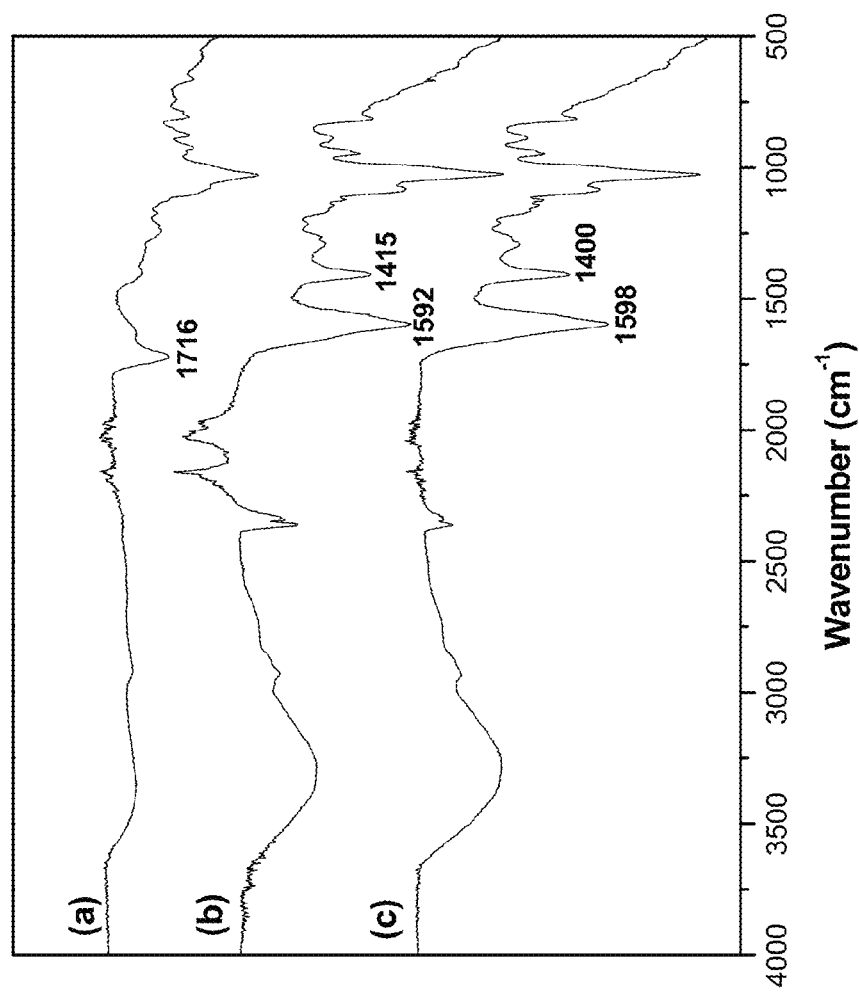
FIG. 6 is a diagram that shows FTIR spectrum of modified alginate sulphonate synthesized by conventional method and microwave synthesis.

FIG. 6 shows an FTIR spectrum of unmodified and functionalized alginic acid derivative synthesized through microwave-assisted synthesis. In FIG. 6 the curves are the FTIR spectra of (a) Unmodified alginic acid, ALG-sulphonate synthesized through: (b) Conventional method (c) Microwave synthesis.

EXAMPLE 6

Figure 7A:
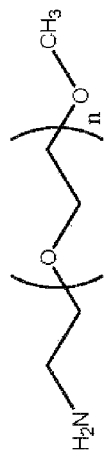
FIG. 7A, FIG. 7B, FIG. 7C is a diagram that shows a chemical synthesis reaction for hydrophilic modification of polygalacturonic acid prepared using amino terminated PEG methyl ether.
Figure 7B:
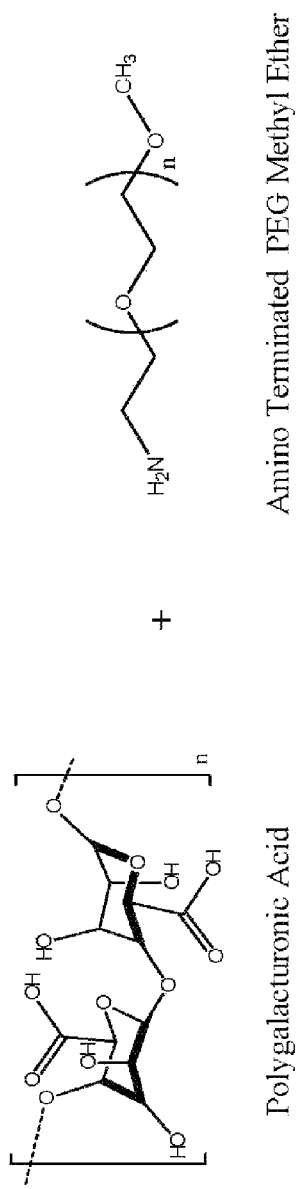
Figure 7C:
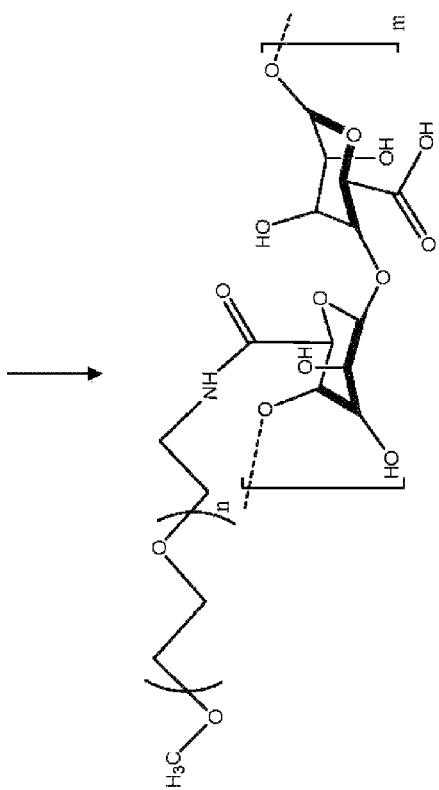

Chemical Synthesis of Hydrophilic Modification of Polygalacturonic Acid Derivative Using Amine Terminated PEG:

Water-insoluble PGA (0.24 mmol) and N-Hydroxysuccinimide (NHS) (28 mg, 0.24 mmol) were dissolved in 10 mL of deionized water. A solution of amine terminated PEG (230 mg, 0.16 mmol in 1 mL deionized water) was added. After stirring for 15 min at room temperature, 330 mg of EDC was added and stirring was continued for 30 min, followed by addition of NaOH (120 µL, 6 M) and 10 min incubation. Purification was achieved by dialysis against distilled water for 4 days (molecular weight cut off 14,000 g/mol). The purified polymer solution was filtered and lyophilized or rotary evaporated at reduced pressures. See reaction scheme in FIG. 7A, FIG. 7B, FIG. 7C, which shows the hydrophilic modification of polygalacturonic acid (PGA) using amino terminated. Polyethylene glycol methyl ether.

EXAMPLE 7

Hydrophilic Modification of Chitosan Derivative, Trimethylammonium Chitosan Chloride (TMC)

In a 50 mL round bottom flask equipped with a reflux condenser, 0.300 mmol of TMC was added to 8 mL of N-Methyl-2-pyrrolidone (NMP) and 1.1 mL of a 15 wt % solution of Sodium Hydroxide (NaOH). The reaction was heated to 80° C., at which time 1.1 mL of Iodomethane was added. The reaction was allowed to proceed for 1.5 hours. Once cooled to room temperature, TMC was precipitated in cold ethanol, isolated via filtration, and dried overnight in a vacuum oven at 50° C. Ion exchange between $I^-$ and $Cl^-$ was done by dissolving TMC in a solution of NaCl, followed by reprecipitation in ethanol.

EXAMPLE 8

Further Modification of Chitosan Derivative Trimethylammonium Chitosan Chloride (TMC)

In a 100 mL round bottom flask, 100 mg TMC (0.300 mmol) was added. Then to this 25 mL acetonitrile, 46-μL triethylamine and 40.1 μL nonanoyl chloride. The flask was fitted with a glass stopper and left to stir overnight at room temperature. The reaction was poured into excess ethanol and the precipitate was filtered and washed with ethanol several times to eliminate acetonitrile. The final product was dried under vacuum.

EXAMPLE 9

Hydrophobic Modification of Polygalacturonic Acid Derivative:

In the first step, polygalacturonic acid-sulphonate (0.568 mmol) was dissolved in 0.1 M NaOH solution. This solution was then added dropwise to vigorously stirred, Divinylsulfone (DVS) (0.852 mmol). The molar ratio of DVS to hydroxyl group depends on the targeted degree of functionalization. Excess off 1.5 times the hydroxyl groups of the targeted degree of functionalization should be used. This PGA-DVS reaction was allowed to proceed for 3 minutes and then stopped by adjusting to pH 5 with addition of 5.0 M HCl.

In another beaker, fatty alcohol (0.852 mmol), was dissolved in 0.1 M NaOH solution. This was then added dropwise to the vigorously stirred solution of PGA-DVS. This PGA-DVS-fatty-alcohol reaction was then allowed to react for 3 minutes and the reaction was stopped by adjusting to pH 5 with addition of 5.0 M HCl. The product was then washed with hot ethanol to remove unreacted fatty acid. The water-soluble product was dialyzed to remove any unreacted DVS, NaOH, HCl and salt using a Spectra/Pore dialysis membrane (molecular weight cut off of 5000-10000) for 3 days. It was then filtered and dried. See the reaction scheme in FIG. 8A, FIG. 8B, FIG. 8C, FIG. 8D, FIG. 8E, which shows the hydrophobic modification of polygalacturonic acid (PGA) based surfactants.

EXAMPLE 10

Polysaccharide Derivative Demonstrates Acid and Base Stability

Figure 9:
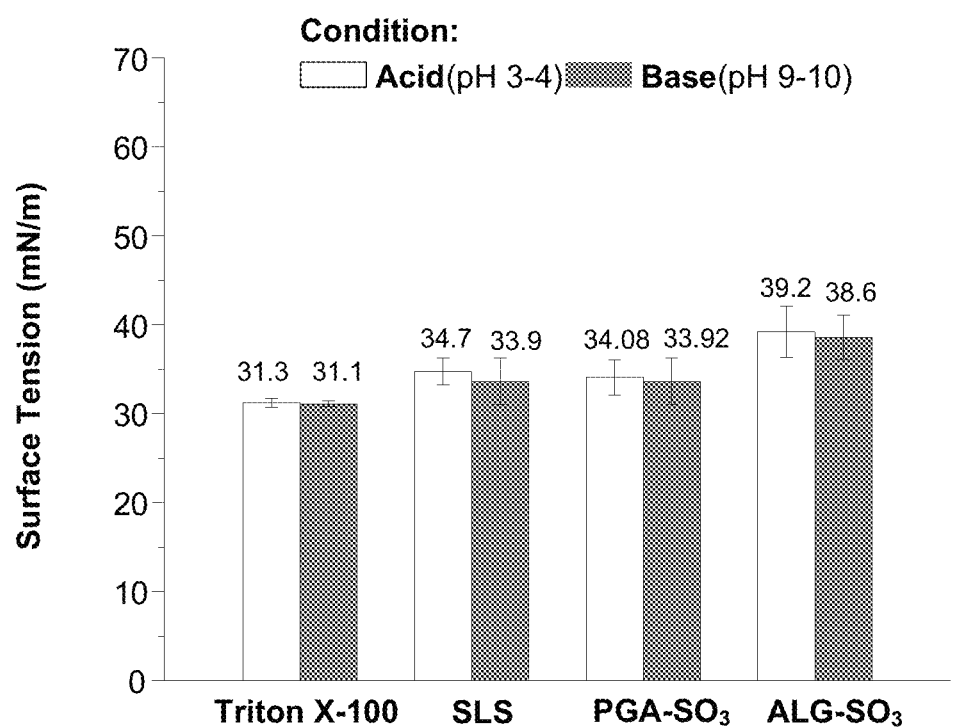
FIG. 9 is a graph that shows the effect of acid and base on the stability of surfactants surface activity.

The stability of the polygalacturonic acid derivative prepared according to this procedure in acid and base conditions is shown in FIG. 9. The derivatives were subjected to acidic and basic medium using hydrochloric acid (HCl) for pH 3-4 and sodium hydroxide (NaOH) for pH 9-10 respectively for 15 days. The surface tension of the derivatives was re-measured after exposure to acidic/basic conditions.

EXAMPLE 11

Polysaccharide Derivative Demonstrates Cleaning Ability Towards Hydrophilic Type Dirt on Glass Substrates The cleaning ability of the polysaccharide derivative was evaluated for standardized cleaning testing in accordance to ASTM G122-96 (2008) "Standard Test Method for Evaluating the Effectiveness of Cleaning Agents". The performance of these modified polysaccharides was compared to commercial surfactants, Triton X-100 and Sodium lauryl sulfate (SLS). Four types of contaminants formulation chosen were bathroom soil, bathroom scum, Hucker's soil and DCC-17 (described below).

The composition of contaminants used to test cleaning ability include:
1. Glass soap scum: Water 51.5%, Hair gel 25.6%, Toothpaste 10.4%, Shaving cream 5.3%, Hair spray 3.7% and Spray deodorant 3.5%.
2. Bathroom soap scum: All-in-one shampoo and conditioner 28.6%, Dry skin lotion 21.4%, Liquid hand soap 21.4%, Liquid body wash 14.3%, Deodorant bar soap 7.2% and Water 7.1%.
3. Hucker's Soil: Distilled water 45.8%, Evaporated milk 13.8%, Creamy peanut butter 9.2%, Salted butter 9.2%, Stone ground wheat flour 9.2%, Egg yolk 9.2%, Printer's ink with boiled linseed oil 0.9% and saline solution 2.7%
4. DCC 17 soil: Mix lard, vegetable oil, vegetable shortening and carbon black.

TABLE 3

Evaluation of Surfactants using Immersion Test (ASTM G122)

| | Contaminant Removed (%) | | | |
|---|---|---|---|---|
| Surfactant | Bathroom Soil | Bathroom Scum | Hucker's Soil | DCC-17 |
| DI Water | 43.2 | 26.9 | 3.69 | 0.15 |
| Triton X-100 | 96.6 | 59.8 | 21.04 | 0.92 |
| SLS | 60.7 | 37.6 | 19.75 | 3.84 |
| PGA-SO3 | 93.0 | 58.5 | 7.32 | 0.84 |

*Measured in 0.1-wt % analyte concentration in 150 mL DI water.

EXAMPLE 12

Polysaccharide Derivative Demonstrates Stain Removal Ability on Fabric

A detergency test of ASTM of D4265-98 'Standard Guide for Evaluating Stain Removal Performance in Home Laundering' and ASTM D4008-95 'Standard Test Method for Measuring Anti-Soil Deposition Properties of Laundry Detergents' were used to measure the cleaning ability of the surfactants on fabric. Contaminant and stain removal efficiency of dirt on cotton fabric was tested and summarized in Table 4.

TABLE 4

Contaminant removal efficiency

| | % Contaminant Removed | |
|---|---|---|
| Surfactant | DI water | Hard Water (150 ppm) |
| DI Water | 12.56 | 17.48 |
| Triton X-100 | 29.30 | 36.25 |
| SLS | 48.06 | 30.17 |
| PGA-SO$_3$ | 46.52 | 27.20 |

The inventions described herein provide the following capabilities and advantages:

A composition of matter comprising a surface-active polymer derived from naturally occurring polysaccharides having structural formulae as shown in FIG. 1A and FIG. 1B that is modified by covalent attachment of hydrophilic moieties (both synthetic and bio-based).

A composition of matter wherein the average molecular weight of the water-insoluble polysaccharide is any value greater than 500.

A composition of matter wherein the average molecular weight of the water-insoluble polysaccharide is preferably in the range of 500 to 150,000.

A composition of matter wherein the polysaccharide contains either hydroxyl, hydroxyl methyl, carboxylic acid, and amine groups at positions $R_1$ and/or $R_2$ as shown in FIG. 1A and FIG. 1B. Examples of water-insoluble naturally occurring polysaccharides include cellulose, chitosan, heparin, polygalacturonic acid, and alginic acid.

A composition of matter wherein water-insoluble naturally occurring polysaccharides are modified using naturally occurring compounds containing sulfonate, amine and/or polyethylene glycol (PEG) or polypropylene glycol PPG) homopolymers and copolymers functionality. Examples of naturally occurring compounds used as hydrophilic modification agents include amino acids, peptides, and lipids containing sulfonate and/or amine groups and polyethylene glycols.

A composition of matter wherein water-insoluble naturally occurring polysaccharides are modified using naturally occurring compounds containing sulfonate, amine and/or polyethylene glycol (PEG) or polypropylene glycol (PEG) homopolymers and copolymers functionality. Examples of naturally occurring compounds used as hydrophilic modification agents include amino acids, peptides, and lipids containing sulfonate and/or amine groups and polyethylene glycols.

A composition of matter comprising a naturally occurring water-insoluble polysaccharide reacted using a chemical catalyst as shown in FIG. 2A, FIG. 2B, FIG. 2C. It is still. In some embodiments, the present invention to provide environmentally safe and mild synthetic route over the prior art for the synthesis of bio-surfactants, based on naturally occurring water-insoluble polysaccharide using a chemical catalyst as shown in FIG. 2A, FIG. 2B, FIG. 2C.

A composition of matter comprising coupling agents selected from the group consisting of EDCL, 1-ethyl-3-(3-dimethylaminopropyl)carbodiimide, other carbodiimides such as DCC, PIC, PEC, EDC, EDC-HC, Uronium/aminium salts, Inunonium salts and Phosphonium-based coupling reagents. See example 1, 2 and 6 which describes use of EDCL.

In some embodiments, the synthesis of these surface-active polymers can also be catalyzed by enzymes or heat provided by conventional means or microwave irradiation as described in example 3, 4 and 5.

The covalent functionalization of the polysaccharides may include but are not limited to amidation, amination, esterification, etherification, alkylation and sulfonation as described in the example section.

In some embodiments, the enzymes that can catalyze the modification include but are not limited to lipase, protease, amylase, carboxylic-ester hydrolases, pectinase and aminases as described in the example 3.

In some embodiments, the present invention provides methods to hydrophilically modify polysaccharides in order to facilitate subsequent hydrophobic functionalization of the polysaccharides.

In some embodiments, the present invention allows the control the hydrophilic and hydrophobic (or lipophilic) balance [HLB] of the polysaccharides by controlling the percentage of hydrophilic and hydrophobic (or lipophilic) groups in the bio-surfactant.

A hydrophilic modification method that can be carried out by using compounds containing sulfonate, amine and/or polyethylene glycol (PEG) or polypropylene glycol (PPG) homopolymers and copolymers functionality. See example 1-7.

A hydrophobic modification method of that can be carried out using naturally occurring fatty acid based-alcohols which includes but is not limited to lauryl alcohol, stearyl alcohol and fatty alcohols ranging from carbon 8 to carbon 22. See example 9 for hydrophobic modification using fatty alcohol.

A subsequent hydrophobic functionalization process that can be performed by using fatty alcohol as shown in FIG. 8A, FIG. 8B, FIG. 8C, FIG. 8D, FIG. 8E and explained in Example 9.

In some embodiments, the present invention provides an approach as described above for the hydrophilic modification, which results in lower surface tension, comparable to commercial synthetic surfactants; Triton™ X-100and Sodium Lauryl Sulfate (SLS). Table 1 summarizes the surface activity of unmodified polysaccharide and polysaccharide derivatives of polygalacturonic acid and alginic acid.

THEORETICAL DISCUSSION

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A composition of matter, comprising:
   a reaction product of a naturally occurring polysaccharide having a backbone structure comprising a plurality of monomer units, each monomer unit having at least one of a carboxylic group or an amine group and having at least one hydroxyl group, wherein said naturally occurring polysaccharide is selected from the group consisting of a polysaccharide derivative of polygalacturonic acid, and a polysaccharide derivative of alginic acid; and a hydrophilic moiety configured to react with some of said at least one of a carboxylic group or an amine group of said naturally occurring polysaccharide, said hydrophilic moiety being 2-aminoethanesulfonate (taurine);

said reaction product retaining said backbone structure and having surface active properties in liquids, said reaction product being a non-toxic biodegradable surfactant that when present in water is configured to reduce a surface tension in deionized water of 73.02 mN/m to a surface tension in the range of 36.08 mN/m to 33.49 mN/m measured in 0.1% analyte concentration at 24° C. using the Du Noüy ring method.

2. The composition of matter of claim 1, comprising a further reaction product retaining said backbone structure and having some of said at least one hydroxyl or one carboxylic acid group of said naturally occurring polysaccharide substituted with a hydrophobic or a lipophilic moiety, said hydrophobic or said lipophilic moiety comprising a selected one of lauryl alcohol, stearyl alcohol, and a saturated fatty alcohol of chain length in the range from $C_5$ to $C_{22}$.

3. The composition of matter of claim 2, wherein said hydrophobic or said lipophilic moiety is a naturally occurring fatty alcohol.

4. A method of making a composition of matter, comprising the steps of:

providing a naturally occurring polysaccharide having a backbone structure comprising a plurality of monomer units, each monomer unit having at least one of a carboxylic group or an amine group and having at least one hydroxyl group, wherein said naturally occurring polysaccharide is selected from the group consisting of a polysaccharide derivative of polygalacturonic acid, and a polysaccharide derivative of alginic acid;

reacting said naturally occurring polysaccharide with a hydrophilic moiety that substitutes for some of said at least one of a carboxylic group or an amine group of said naturally occurring polysaccharide, said hydrophilic moiety being 2-aminoethanesulfonate (taurine); and recovering a reaction product that retains said backbone structure and is surface active in liquids, said reaction product when present in water is configured to reduce a surface tension in deionized water of 73.02 mN/m to a surface tension in the range of 36.08 mN/m to 33.49 mN/m measured in 0.1% analyte concentration at 24° C. using the Du Noüy ring method.

5. The method of making a composition of matter of claim 4, wherein said reacting step is performed using applied microwave energy.

6. The method of making a composition of matter of claim 4, wherein said reacting step is performed using thermal energy.

7. The method of making a composition of matter of claim 4, wherein said reacting step involves a catalyst.

8. The method of making a composition of matter of claim 4, further comprising the steps of:

reacting said reaction product that retains said backbone structure with a hydrophobic or lipophilic moiety that substitutes for some of said at least one of a hydroxyl group or carboxylic acid group of said naturally occurring polysaccharide; and recovering a second reaction product that retains said backbone structure and has both hydrophilic and hydrophobic/lipophilic properties.

9. The method of making a composition of matter of claim 8, wherein said hydrophobic or lipophilic moiety is a naturally occurring fatty alcohol.

10. The method of making a composition of matter of claim 9, wherein said naturally occurring fatty alcohol is a selected one of lauryl alcohol, stearyl alcohol, and a saturated fatty alcohol of chain length in the range from $C_5$ to $C_{22}$.

11. The composition of matter of claim 1, wherein said polysaccharide has a molecular weight in the range of 500 to 150,000 daltons.

12. The composition of matter of claim 2, wherein said polysaccharide has a molecular weight in the range of 500 to 150,000 daltons.

* * * * *